(12) United States Patent
Caduff et al.

(10) Patent No.: US 9,247,905 B2
(45) Date of Patent: Feb. 2, 2016

(54) WIDE BAND FIELD RESPONSE MEASUREMENT FOR GLUCOSE DETERMINATION

(75) Inventors: Andreas Caduff, Zürich (CH); Mark Stuart Talary, Zürich (CH); Martin Müller, Federnstrasse (CH); Oscar De Feo, Lausanne (CH)

(73) Assignee: BIOVOTION AG, Zurich (CH)

(*) Notice: Subject to any disclaimer, the term of this patent is extended or adjusted under 35 U.S.C. 154(b) by 754 days.

(21) Appl. No.: 13/264,788

(22) PCT Filed: Apr. 17, 2009

(86) PCT No.: PCT/CH2009/000122
§ 371 (c)(1),
(2), (4) Date: Dec. 28, 2011

(87) PCT Pub. No.: WO2010/118538
PCT Pub. Date: Oct. 21, 2010

(65) Prior Publication Data
US 2012/0101351 A1    Apr. 26, 2012

(51) Int. Cl.
*A61B 5/02*    (2006.01)
*A61B 5/00*    (2006.01)
(Continued)

(52) U.S. Cl.
CPC .......... *A61B 5/4869* (2013.01); *A61B 5/0507* (2013.01); *A61B 5/0531* (2013.01); *A61B 5/0537* (2013.01); *A61B 5/1455* (2013.01); *A61B 5/14532* (2013.01); *A61B 5/01* (2013.01); *A61B 2560/0252* (2013.01); *A61B 2562/0209* (2013.01); *A61B 2562/043* (2013.01); *A61B 2562/046* (2013.01)

(58) Field of Classification Search
CPC .................................................. A61B 5/14532
USPC ...................... 600/345, 347, 365; 204/403.01
See application file for complete search history.

(56) References Cited

U.S. PATENT DOCUMENTS

| 4,509,531 A | 4/1985 | Ward |
| 5,050,612 A | 9/1991 | Matsumura |

(Continued)

FOREIGN PATENT DOCUMENTS

| JP | 10-137193 A | 5/1998 |
| JP | 2007-527248 A | 9/2007 |

(Continued)

OTHER PUBLICATIONS

International Search Report dated Jun. 23, 2010 and an International Preliminary Report on Patentability dated Oct. 27, 2011 for Application No. PCT/CH2009/000122.

(Continued)

*Primary Examiner* — Patricia Mallari
*Assistant Examiner* — Vasuda Ramachandran
(74) *Attorney, Agent, or Firm* — Ladas & Parry LLP

(57) ABSTRACT

A method and device for determining the glucose level in living tissue are based on measuring the response of the tissue an electric field as well as temperature measurements. In order to improve accuracy, it has been found that measurements in at least three frequency ranges between 1 kHz and 200 kHz, 0.2 MHz an 100 MHz as well as above 1 GHz should be combined since the response of the tissue in these different frequency ranges is ruled by differing mechanisms.

11 Claims, 4 Drawing Sheets

(51) Int. Cl.
  *A61B 5/05*    (2006.01)
  *A61B 5/053*   (2006.01)
  *A61B 5/145*   (2006.01)
  *A61B 5/1455*  (2006.01)
  *A61B 5/01*    (2006.01)

(56) References Cited

U.S. PATENT DOCUMENTS

| | | | |
|---|---|---|---|
| 5,353,802 A | 10/1994 | Ollmar | |
| 5,779,867 A * | 7/1998 | Shieh | 204/403.12 |
| 5,792,668 A | 8/1998 | Fuller et al. | |
| 5,890,489 A | 4/1999 | Elden | |
| 6,175,752 B1 | 1/2001 | Say et al. | |
| 6,309,884 B1 | 10/2001 | Cooper et al. | |
| 6,517,482 B1 | 2/2003 | Elden et al. | |
| 6,762,609 B2 | 7/2004 | Alanen et al. | |
| 6,849,046 B1 | 2/2005 | Eyal-Bickels et al. | |
| 2003/0036674 A1 | 2/2003 | Bouton | |
| 2004/0065158 A1 | 4/2004 | Schrepfer et al. | |
| 2004/0249421 A1 * | 12/2004 | Harel et al. | 607/40 |
| 2005/0043602 A1 | 2/2005 | Freger et al. | |
| 2005/0192488 A1 | 9/2005 | Bryenton et al. | |
| 2005/0203361 A1 | 9/2005 | Caduff et al. | |
| 2006/0025664 A1 | 2/2006 | Kim et al. | |
| 2007/0055117 A1 * | 3/2007 | Alphonse | 600/310 |
| 2007/0161881 A1 | 7/2007 | Ollmar et al. | |
| 2007/0282180 A1 | 12/2007 | Caduff et al. | |
| 2008/0039718 A1 * | 2/2008 | Drinan et al. | 600/427 |
| 2008/0057526 A1 | 3/2008 | Caduff et al. | |
| 2008/0319285 A1 | 12/2008 | Hancock | |
| 2009/0312615 A1 | 12/2009 | Caduff et al. | |
| 2010/0099960 A1 | 4/2010 | Caduff et al. | |
| 2010/0130883 A1 | 5/2010 | Carpenter et al. | |
| 2010/0240977 A1 | 9/2010 | Caduff | |
| 2010/0298680 A1 | 11/2010 | Talary et al. | |
| 2010/0324398 A1 | 12/2010 | Tzy-Ping | |
| 2011/0144525 A1 | 6/2011 | Megej et al. | |
| 2011/0160554 A1 | 6/2011 | Megej et al. | |

FOREIGN PATENT DOCUMENTS

| | | | |
|---|---|---|---|
| JP | 2009-514619 A | 4/2009 | |
| WO | 96/32883 A1 | 10/1996 | |
| WO | 99/44495 A1 | 9/1999 | |
| WO | 00/09996 A1 | 2/2000 | |
| WO | WO 02/069791 A1 * | 9/2002 | A61B 5/05 |
| WO | 03/052865 A2 | 6/2003 | |
| WO | 2004/023125 A2 | 3/2004 | |
| WO | 2005/053526 A1 | 6/2005 | |
| WO | WO 2005/053523 A1 * | 6/2005 | A61B 5/14532 |
| WO | WO 2005/053526 A1 * | 6/2005 | A61B 5/7239 |
| WO | WO 2005/120332 A1 * | 12/2005 | A61B 5/0531 |
| WO | WO 2007/053963 A1 * | 5/2007 | A61B 5/721 |
| WO | 2008/141306 A2 | 11/2008 | |
| WO | 2010/105373 A1 | 9/2010 | |

OTHER PUBLICATIONS

A. Caduff et al., First human experiments with a novel non-invasive, non-optical continuous glucose monitoring system, Biosensor and Bioelectronics 19 (2003), 209-217.

A.H. Lackermeier et al., In Vivo ac Impedance Spectroscopy of Human Skin, XP008029774, 197-213.

V.V. Meriakri et al., Dielectric Properties of Water Solutions with small Content of Glucose in the Millimeter-Wave Band and the Determination of Glucose in Blood, MSMW'07 Symposium Proceedings, Kharkov, Ukraine, Jun. 25-30, 2007, 1-4244-1237-4/07/$25.00 © 2007 IEEE, 873-875.

K. Fuchs and U. Kaatze, Molecular Dynamics of Carbohydrate Aqueous Solutions. Dielectric Relaxation as a Function of Glucose and Fructose Concentration, 1. Phys. Chem. B 2001,105, 2036-2042.

Omar S. Khalil, Ph.D., Non-Invasive Glucose Measurement Technologies: An Update from 1999 to the Dawn of the New Millennium, Diabetes Technology & Therapeutics, vol. 6, No. 5, 2004, © Mary Ann Liebert, Inc., 660-695.

B.C. Lesieutre et al., Forward and Inverse Parameter Estimation Algorithms of Interdigital Dielectrometry Sensors, IEEE Transactions on Dielectrics and Electrical Insulation vol. 8 No. 4, Aug. 2001, 577-588.

F. Dewarrat et al., Measurement and Simulation of Conductive Dielectric Two-layer Materials with a Multiple Electrodes Sensor, 1070-9878/08/$25.00 © 2008 IEEE, 1406-1414.

M.S. Talary, et al., An RCL Sensor for Measuring Dielectrically Lossy Materials in the MHz Frequency Range, IEEE Transactions on Dielectrics and Electrical Insulation vol. 13, No. 2; Apr. 2006, 247-256.

Daniel Huber et al., The compensation of perturbing temperature fluctuation in glucose monitoring technologies based on impedance spectroscopy, Med Bio Eng Comput (2007) 45, 863-876.

Mark S. Talary et al., In vivo life sign application of dielectric spectroscopy and noninvasive glucose monitoring, Elservier Journal of Non-Crystalline Solids 353 (2007), 4515-4517.

Andreas Caduff et al., Non-invasive glucose monitoring in patients with Type 1 diabetes: A Multisensor system combining sensor for dielectric and optical characterization of skin, Biosensor and Bioelectronics 24 (2009), 2778-2784.

Andreas Caduff et. al., Multisensor Concept for non-invasive Physiological Monitoring, Instrumentation and Measurement Technology Conference—IMTC 2007 Warsaw, Poland, May 1-3, 2007, 1-4.

A. Kraszewski et al., Dielectric properties and a model of biphase water suspension at 9.4 GHz, Journal of Applied Physics, vol. 47, No. 4, Apr. 1976, 1275-1277.

Office Action dated Aug. 20, 2013 for Application No. JP 2012-505014.

espacenet English abstract of JP 2009-514619 A dated Sep. 10, 2013.

espacenet English abstract of JP 10-137193 A dated Sep. 10, 2013.

* cited by examiner

WIDE BAND FIELD RESPONSE MEASUREMENT FOR GLUCOSE DETERMINATION

TECHNICAL FIELD

The invention relates to a device and method for determining the glucose level of living tissue. In particular, it relates to technologies that derive the glucose level from the response of the tissue to an applied electrical field.

BACKGROUND ART

WO 02/069791 describes a device for determining the glucose level of living tissue. The device comprises an electrode arrangement mounted to a substrate, as well as a control unit adapted to determine the response of the tissue to the electric field generated by the electrodes. This type of device exploits the fact that the glucose level affects the dielectric and electric response of the same.

Similarly, WO 2005/053523 and WO2005/053526 describe hardware and measurement methodology to be used in such a device.

Since glucose level is not the only state variable of the tissue that affects its electric and dielectric response, accuracy with such device can only be achieved by measuring and combining appropriate measured parameters.

DISCLOSURE OF THE INVENTION

The problem to be solved by the present invention is therefore to provide an improved device and method of this type that allows a more accurate glucose level determination.

This problem is solved by the device and method of the independent claims.

Accordingly, AC signal voltages of at least a first, a second and a third frequency are applied, consecutively or simultaneously, to the electrode arrangement in order to measure a first, a second and a third electric parameter, respectively. The first frequency is between 1 kHz and 200 kHz, the second frequency is between 0.2 MHz and 100 MHz, and the third frequency is at least 1 GHz.

In addition, a temperature parameter indicative of the temperature of the tissue is measured.

The first, second and third electric parameter as well as the temperature parameter are then combined in order to derive the glucose level. For example, a sum of linear and/or quadratic terms of the first, second and third electric parameter and the temperature signal can be used, with coefficients obtained from calibration measurements.

This is based on the understanding that measurements in the three specific frequency ranges are advantageous in order to eliminate the influence of tissue state parameters other than glucose on the measured signals. For example, glucose mainly modulates the beta-dispersion in the frequency range 0.2 MHz to 100 MHz, and the effect of sweat can be eliminated because it primarily affects the signal in the frequency range between 1 kHz and 200 kHz, while it has a lesser effect on the signals at the other frequency ranges. Furthermore, the temperature of the tissue affects all the electrically measured parameters, therefore a direct temperature measurement allows to improve the accuracy further.

Advantageously, in order to compensate for changes in the water content in the skin and underlying tissue, the third frequency should be between 1 GHz and 30 GHz because the dielectric response of water primarily affects the signal in this frequency range, while it has a lesser effect on the signals at the other frequency ranges.

In a further advantageous embodiment, the first electric parameter is measured by means of a first pair of electrodes designed as interdigital electrodes because the separation gap needs to be very small to allow measuring only surface effects, and the interdigital arrangement allows for a suitable large measurement surface.

The second electric parameter is best measured by means of a second pair of electrodes separated by a gap of at least 2 mm. This allows to generate a field reaching sufficiently far into the tissue in order to measure the beta-dispersion of blood in the tissue. Advantageously, at least two pairs of electrodes with different gap widths are provided for measurements at the second frequency range. They are used for measuring at least two different electric parameters, which allows to obtain depth-resolved information. The two pairs of electrodes may have one electrode (e.g. the ground electrode) in common.

The third electric parameter is also best measured by means of a dedicated third pair of electrodes, which can be optimized for measurements at the Gigahertz range, e.g. be being designed as coplanar waveguides. Advantageously, at least two pairs of electrodes with different gap widths are provided for measurements at the third frequency range. They are used for measuring at least two different electric parameters, which again allows to obtain depth-resolved information. The two pairs of electrodes may also have one electrode (e.g. the ground electrode) in common.

The following parameters are found to be particularly indicative for a glucose measurement:

p1—a value depending on the phases of the impedances measured at several frequencies in the second frequency range at frequencies larger than 30 MHz, measured by means of an electrode having a separation gap of at least 2 mm. Advantageously, if the parameters are subsequently combined using linear or quadratic combinations, the logarithms of the phases of the impedances are used.

p2—a value depending on the phases of the impedances measured at several frequencies in the second frequency range at frequencies larger than 30 MHz, measured by means of an electrode pair having a separation gap of less than 2 mm. Advantageously, if the parameters are subsequently combined using linear or quadratic combinations, logarithms of the phase of the phases of the impedances are used.

p3—a value depending on the phases of the impedances measured at several frequencies in the first frequency range at frequencies larger than 100 kHz. Advantageously, if the parameters are subsequently combined using linear or quadratic combinations, logarithms of the phase of the phases of the impedances are used.

p4—a value depending on the magnitudes of the impedances measured at several frequencies in the first frequency range at frequencies larger than 100 kHz. Advantageously, if the parameters are subsequently combined using linear or quadratic combinations, logarithms of the phase of the phases of the impedances are used.

p5—a value depending on the phases of the transmission coefficient measured at least one frequency f1 in the third frequency range, measured by means of an electrode having a separation gap of at least 1 mm. Advantageously, if the parameters are subsequently combined using linear or quadratic combinations, the square of the phase of the transmission is used.

p6—a value depending on the phases of the transmission coefficient measured at least one frequency f2 in the third frequency range, measured by means of an electrode having a separation gap of less than 1 mm. Advantageously, if the parameters are subsequently combined using linear or quadratic combinations, the square of the phase of the transmission is used.

p7—a value depending on the temperature.

In addition to this, the measurement can further be refined by also taking into account at least one of the following parameters p8—a value depending on the phases of the impedances measured at several frequencies in the second frequency range between 10 and 30 MHz, measured by means of an electrode having a separation gap of at least 2 mm. Advantageously, if the parameters are subsequently combined using linear or quadratic combinations, the logarithms of the phases of the impedances are used.

p9—a value depending on the phases of the impedances measured at several frequencies in the second frequency range between 10 and 30 MHz, measured by means of an electrode having a separation gap of less than 2 mm. Advantageously, if the parameters are subsequently combined using linear or quadratic combinations, the logarithms of the phases of the impedances are used.

p10—a value depending on the magnitude of the impedances measured at several frequencies in the second frequency range at frequencies smaller than 10 MHz, measured by means of an electrode having a separation gap of at least 2 mm. Advantageously, if the parameters are subsequently combined using linear or quadratic combinations, the logarithms of the magnitudes of the impedances are used.

p11—a value depending on the magnitudes of the impedances measured at several frequencies in the second frequency range at frequencies smaller than 10 MHz, measured by means of an electrode having a separation gap of less than 2 mm. Advantageously, if the parameters are subsequently combined using linear or quadratic combinations, the logarithms of the magnitudes of the impedances are used.

p12—a value depending on the magnitudes of the transmission coefficient measured at least one frequency f1'<f1 in the third frequency range, measured by means of an electrode having a separation gap of at least 1 mm. Advantageously, if the parameters are subsequently combined using linear or quadratic combinations, the square of the magnitude of the transmission is used.

p13—a value depending on the magnitudes of the transmission coefficient measured at least one frequency f2'<f2 in the third frequency range, measured by means of an electrode having a separation gap of less than 1 mm. Advantageously, if the parameters are subsequently combined using linear or quadratic combinations, the square of the magnitude of the transmission is used.

Advantageously, when calculating the glucose level, the parameters are weighted with weights, with part of said weights being "global weights", which are defined as weights that are common for a series of devices, i.e. which do not have to be adapted to the individual user. Another part of the weights are "user weights", which are defined as weights that have to be calibrated for individual users. At least the following parameters are advantageously weighted by means of global weights:

p1, p2, p3, p4, p7, and, where applicable, p10, p11

In addition to this, or alternatively, at least the following parameters are advantageously weighed by means of local weights:

p5, p6, and, where applicable, p8, p9, p12, p13.

This is due to the fact that the parameters p5, p6 and, where applicable, p12, p13 mainly account for the changes in water content in the biological tissue, these are proportional to its thickness and may change from case to case. Furthermore, where applicable, the parameters p8 and p9 mainly account for the electrical losses in the biological tissue, which are again proportional to tissue thickness.

For example, the glucose level can be calculated using a linear, weighted sum and an offset, i.e. using a term such as $$c + \sum_{i=1}^{N} k_i \cdot p_i,$$

wherein c is an offset, $k_i$ are weights, $p_i$ are the measured parameters and N is the number of measured parameters.

At least some of the weights $k_i$ can be determined in calibration measurements. Advantageously, such calibration measurements comprise a calibration step where the parameters and a series of reference glucose values are measured over an extended period of time. In this context, a "reference glucose value" is a glucose level determined by other means than by means of the present invention, e.g. by analyzing blood samples, by optical measurements, etc.

During the calibration step, terms of the type $$c_j + \sum_{i=1}^{N} k_i \cdot p_i$$

are calculated, with $c_1, c_2, \ldots, c_J$ being additive values. For a first series of consecutive measurements $c_1$ is used, for a second series of consecutive measurements $c_2$ is used, etc. In other words, the series of measurements is divided into sub-series, with each sub-series j having its own additive value $c_j$. Then, all the additive values $c_j$ and at least part of the parameters $k_i$ are fitted to the reference glucose values. The use of several additive values allows to compensate for a drift in the measurement by minimizing the effect of this latter in the estimation of the parameters $k_i$.

After this calibration step, the determination of the glucose level in "normal" operation can e.g. comprise the following steps:

measurement of a reference glucose value, i.e. in the morning, determination of the offset c from the reference glucose value and the weights obtained in the calibration step, and for subsequent measurements, e.g. during the day, determination of the glucose level from the measured parameters, the weights obtained in the calibration step, and the offset c.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

General Hardware Design

Figure 1:
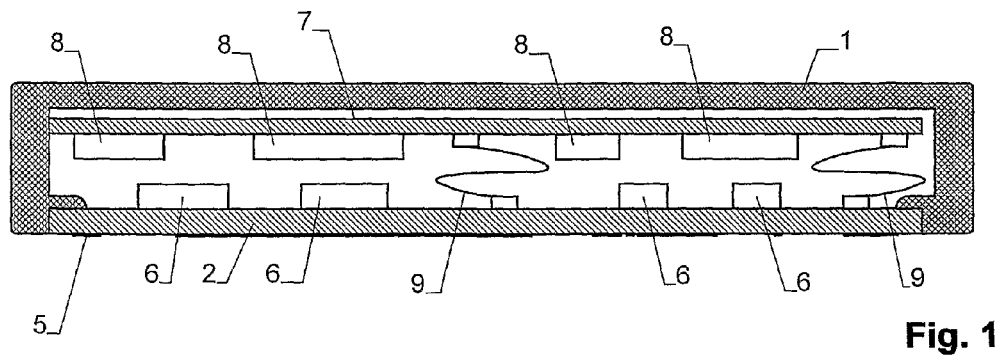
FIG. 1 shows a sectional view of a device.
Figure 2:
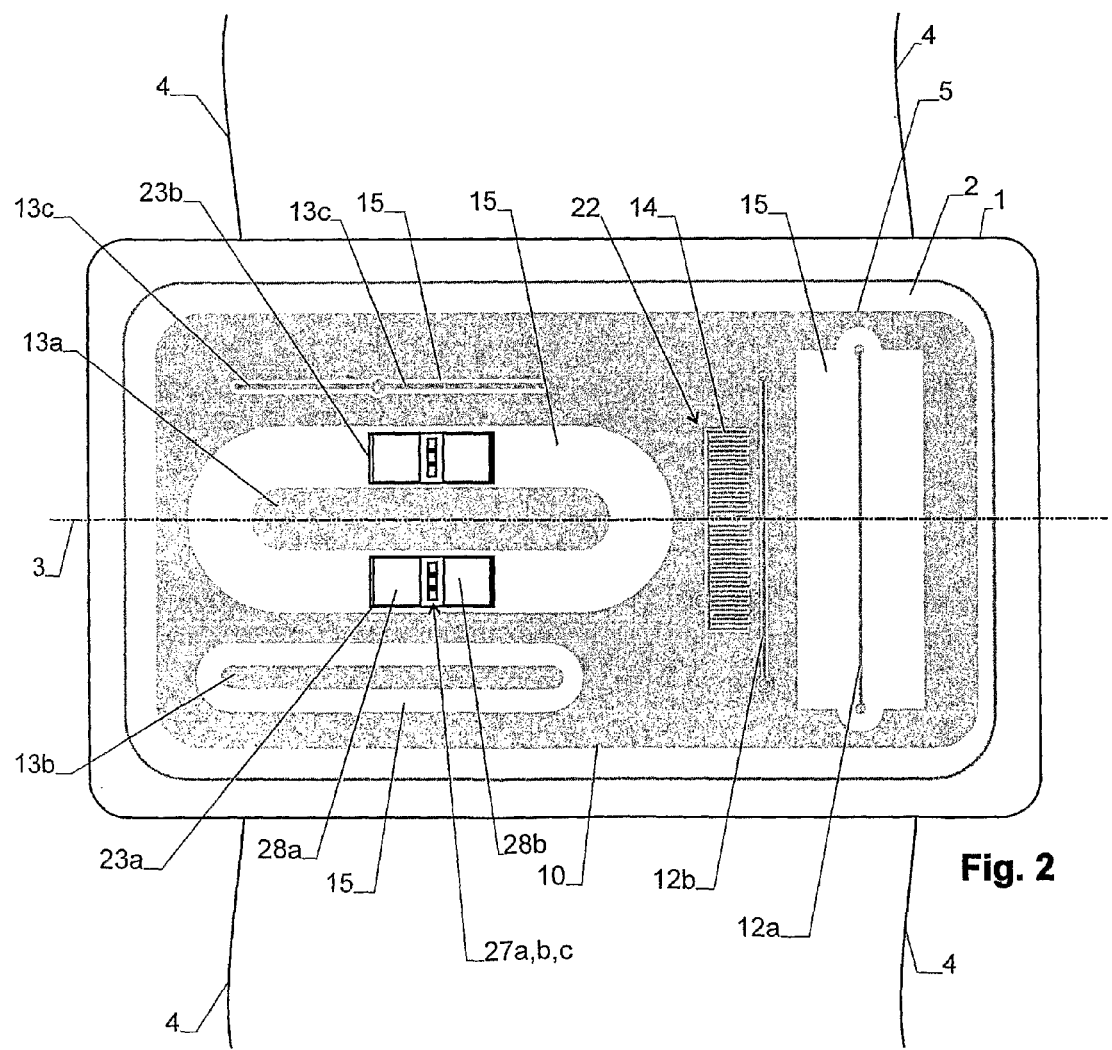
FIG. 2 shows a bottom view of the device of FIG. 1.

The general design of an advantageous embodiment of the device is shown in FIGS. 1 and 2. The device comprises a housing 1, e.g. of plastics. One side of the device, in the following called the "bottom side", is closed by a substrate 2. Substrate 2 is rectangular and elongate and has a longitudinal axis 3. A band or wristband 4 is attached to housing 1, extends perpendicular to longitudinal axis 3 and allows to mount the device e.g. to an arm or leg of a person, with longitudinal axis 3 extending parallel to the longitudinal axis of the arm or leg.

At a first side (bottom side) substrate 2 carries an electrode arrangement formed by a structured metal layer 5. Metal layer 5 is shown in gray in FIG. 2. On its second side (top side) electronic components 6 are mounted to substrate 2 and connected to metal leads on the surface or within substrate 2.

Housing 1 encloses at least one printed circuit board 7 in addition to substrate 2, which carries further electronic components 8. Electrical connectors 9 are provided for connecting printed circuit board 7 to substrate 2.

In addition, the device typically also contains a battery as well as interface and/or display components (not shown).

As mentioned, substrate 2 has a first (bottom) side and a second (top) side, with the first side being applied to a person's skin during operation of the device.

Metal layer 5 is structured to form a ground electrode 10 having openings. Signal electrodes 12a, 12b, 13a, 13b, 13c and 14 are placed within these openings, such that gaps 15 are formed between the inner edges of the openings and the outer edges of the signal electrodes. Each signal electrode 12a, 12b, 13a, 13b, 13c and 14 is completely surrounded by such a gap 15.

The electrode arrangement can comprise an optional dielectric layer covering metal layer 5 for mechanically and/or chemically protecting the electrodes.

During a measurement, the device is worn with the electrode arrangement applied against the tissue, i.e. the skin of the user.

Electrodes

There are three sets of signal electrodes:

A first set of signal electrodes 14 are comprised of interdigital electrodes 22 and are operated at the first frequency range between 1 kHz and 200 kHz.

A second set of signal electrodes 13a, 13b, 13c are operated as capacitive sensors in the second frequency range, i.e. between 0.2 MHz and 100 MHz.

A third set of signal electrodes 12a, 12b are operated as "coplanar waveguides" (CPW) at frequencies in the third frequency range of at least 1 GHz.

Each signal electrode 12a, 12b, 13a, 13b, 13c, 14 forms an electrode pair together with ground electrode 10.

The primary purpose of the first set of signal electrodes 14 is the measurement of sweat and moisture, as described in section 2.2 of WO 2007/053963. The signal from the signal generator is fed to a contact point in the center of signal electrode 14, and a signal depending on the impedance Z between the signal electrode and the ground electrode is measured, as described in WO 2007/053963.

The width of the fingers of the interdigital electrodes as well their mutual distance is advantageously in the order of 0.15 mm.

The electrodes 13a, 13b, 13c of the second set are strip-shaped. The signal from the signal generator is fed to a contact point in the center of the signal electrode, and a signal depending on the impedance Z between the signal electrode and the ground electrode is measured, as e.g. described in WO 2007/053963 or WO 2005/053523.

Differing electrode geometries are used in order to generate electric fields reaching into different depths of the tissue. Hence, the widths of the gaps 15 around the signal electrodes 13a, 13b, 13c differ. Advantageously: for signal electrode 13a, the width of the gap as well as the width of the signal electrode are typically 4 mm, for signal electrode 13b the width of the gap as well as the width of the signal electrode are typically 1.5 mm, and for signal electrode 13b the width of the gap as well as the width of the signal electrode are typically 0.3 mm. The length of the signal electrodes 13a, 13b, 13c should be as large as possible in order to have a large measured volume of skin and underlying tissue.

The signal electrodes 13a, 13b, 13c extend parallel to each other and parallel to the longitudinal axis 3, which increases the interaction length between the electrodes and the tissue within the wearer's arm or leg.

Each signal electrodes 12a, 12b of the third set forms a conductor-backed coplanar waveguide together with the surrounding part of ground electrode 10 and a shield electrode embedded within or arranged on the opposite side of substrate 2. The signal from the signal generator is fed to a first end of the signal electrode and the signal at the second, opposite end is fed to a signal detector, which will be described below.

Again, as described in WO 2005/120332 and WO 2007/053963, it is advantageous to generate electric fields reaching into different depths of the tissue, for which purpose the width of the gaps around the signal electrodes 12a and 12b differ. Advantageously: for signal electrode 12a, the width of the gap is typically up to 4 mm, for signal electrode 12b the width of the gap is typically up to 0.15 mm. Both signal electrodes 12a, 12b have a width of 0.2 mm or less and a length of 20-23 mm.

The signal electrodes 12a, 12b of the third set are parallel to each other and extend perpendicularly to longitudinal axis 3. It has been found that for high-frequency sensors of this type, an arrangement perpendicular to the arm/leg of the wearer provides more robust measurements that are less prone to signal errors due to mechanical shifts related to sensor contact with the skin. However, the signal electrodes 12a, 12b may also extend parallel to longitudinal axis 3.

Optical Sensors

As described in WO 2007/053963, it is advantageous to combine the electrical measurements with optical measurements, in particular optical reflectance measurements. For this purpose, the device can be equipped with at least one optical reflection sensor. Such a sensor allows to obtain a measure of the perfusion of the tissue.

In the embodiment of FIG. 2, the device comprises two such optical reflection sensors 23a and 23b. Each optical reflection sensor 23a, 23b is arranged in the gap around signal electrode 13a.

Each optical reflection sensor 23a, 23b advantageously comprises at least one light source and at least one light detector. In the embodiment shown in FIG. 2, each optical reflection sensor comprises three light sources 27a, 27b, 27c arranged in a row that extends perpendicularly to the longitudinal axis of the sensor. The light sources 27a, 27b, 27c advantageously emit light in the visible or near-infrared spectral range. Furthermore, in the embodiment of FIG. 2, each optical reflection sensor comprises two light detectors 28a, 28b, with the light sources 27a, 27b, 27c located between the light detectors 28a, 28b, such that the light detectors 28a, 28b are able to sense light scattered in forward as well as backward direction respectively to the longitudinal axis of the sensor but having different separations to the light sources 27a, 27b and 27c allowing for perfusion at different depths in the tissue to be measured.

Using at least two light sources with different optical emission spectra has the advantage that differing tissue processes giving rise to a spectrally differing reflectance changes can be distinguished.

In particular, if two light sources are used, one should generate a wavelength below 600 nm and the other a wavelength above 700 nm, advantageously at approximately 568 nm and 800 nm. If three light sources are used, the first one should advantageously generate light at a wavelength below 600 mm, the second one light of a wavelength above 700 nm, and the third one light at a wavelength between 600 and 700 nm. Advantageous values were found to be 568 nm, 800 nm and 660 nm, respectively. It must be noted that 568 nm and 800 nm are "isosbestic" points where the haemoglobin absorption does not depend on the level of oxygenation. In order to correct for skin perfusion changes, the haemoglobin related signal can be calculated by the ratio of the absorption at 568 nm and 800 nm. The oxygen signal can be calculated at 660 nm, a wavelength where the difference between the absorbance of oxygenated and deoxygenated haemoglobin is at its largest, as a ratio to the 800 nm.

Figure 3:
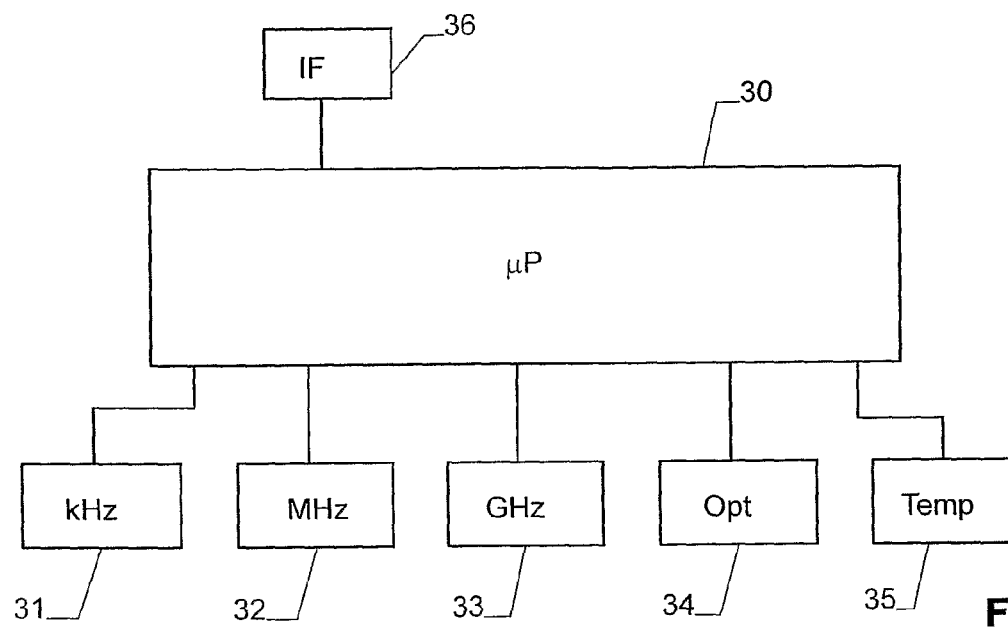
FIG. 3 is a block circuit diagram of the device.

Electronics:

FIG. 3 shows a block diagram of an embodiment of the device. It comprises a control unit 30, e.g. a microprocessor with program and data memory as known to the skilled person, which controls the operation of the device. It is connected to various sensors, in particular:

a) A low-frequency sensor 31 operated by a signal generator and signal detector in the first frequency range, which uses the interdigital electrodes 22 for its measurements.

b) A medium-frequency sensor 32 operated by a signal generator and signal detector in the second frequency range, which uses the second set of signal electrodes 13a, 13b, 13c for its measurements.

c) A high-frequency sensor 33 operated by a signal generator and signal detector in the third frequency range, which uses the third set of signal electrodes 12a, 12b for its measurements.

d) An optical detector 34 measuring optical reflection by means of the optical reflection sensors 23a, 23b.

e) A temperature sensor 35 measuring a temperature of the surface of the tissue as well as, optionally, the temperature within housing 1, e.g. by means of a first temperature sensing device in direct thermal contact with substrate 2, as well as by means of a second temperature sensing device arranged inside housing 1.

Note: In the present embodiment, the signal generators of the low-frequency sensor 31, medium-frequency sensor 32 and high-frequency sensor 33 form the "signal generation circuit" as referred to in the claims.

In addition to the sensors, control unit 30 controls an interface 36 for exchanging data with an external device, which is used for analyzing and displaying the data measured by the present device. It must be noted, though, that this type of functionality can also be incorporated into the present device itself.

Figure 4:
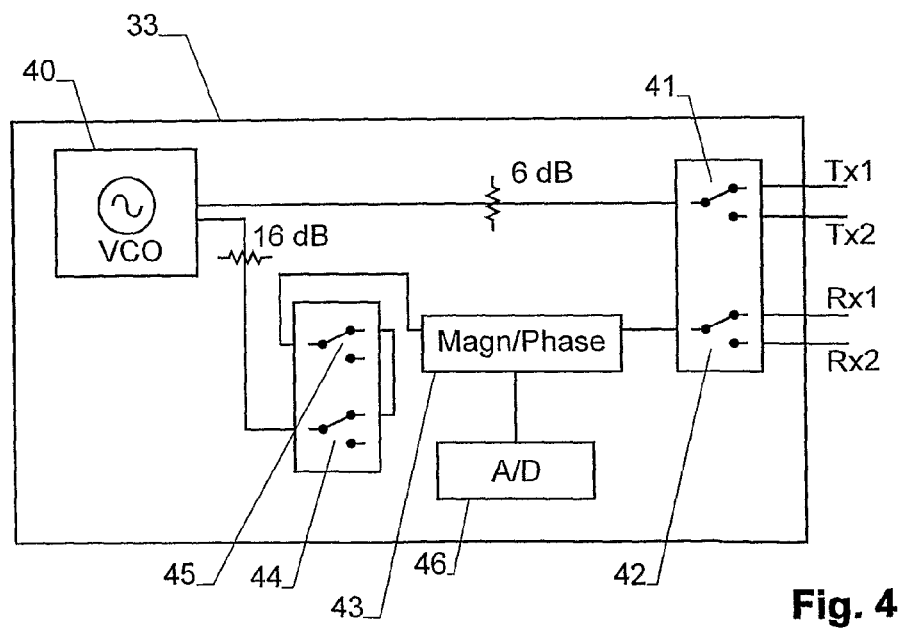
FIG. 4 is a block circuit diagram of the GHz-electronics of the device.

FIG. 4 shows a more detailed diagram of the high-frequency sensor 33. It comprises a voltage-controlled oscillator 40 with two identical outputs. One of the outputs is connected to a first switch 41, from where it is selectively sent to the input end Tx1, Tx2 of one of the signal electrodes 12a, 12b. The appropriate one of the signals Rx1, Rx2 from the output ends of the signal electrodes 12a, 12b is selected with a second switch 42 and fed to a first input of a magnitude/phase detector 43. The other output of oscillator 40 is routed through two static switches 44, 45 of the same type as the switches 41, 42 and then to the second input of magnitude/phase detector 43. The purpose of the static switches 44, 45 is to increase the symmetry of the two signal paths from oscillator 40 to magnitude/phase detector 43 in terms of temperature and technological variations.

Magnitude/phase detector 43 measures the relative magnitude and phase of the signals at its two inputs, which correspond to the complex transmission T of the coplanar waveguide, and feeds the corresponding value to an A/D converter 46.

Glucose Determination

Control unit 30 is structured and adapted by means of software and the above hardware to determine the glucose level g from the measured parameters.

The basic principles of operation of this type of device are described in WO 2007/053963. In most general terms, glucose level g can be determined from the measured parameters $p_i$ with i=1, 2, ... N using a suitable function $f$ as $$g = (f(p_1, \ldots p_N)).$$

In many cases, and in particular when suitably choosing the parameters $p_i$, function $f$ can be a linear or polynomial function in the parameters $p_i$. In a most simple approach, the glucose level can be determined from the measurements of the device described above by means of the following linear combination $$c + k_1 \cdot p_1 + k_2 \cdot p_2 + k_3 \cdot p_3 + k_4 \cdot p_4 + k_5 \cdot p_5 + k_6 \cdot p_6 + k_7 \cdot p_7,$$

where c is an offset constant, to be determined via a reference measurement of glucose performed in the morning and kept constant during the day. The weights coefficient $k_i$ are determined via calibration to reference measurements as described below, and the measured parameters $p_i$ are as follows.

p1—the average or a weighted sum of the logarithms of the phase of the impedance as measured by the signal electrode 13a ("large") of FIG. 1 at the frequencies: 35, 40, and 45 MHz, namely $$p_1 = \frac{1}{3}\sum_{i=1}^{3} \log_{10}(\angle(Z_{el2}(f_i)))$$

$f_i = \{35, 40, 45\}$ MHz, where $\angle(Z)$ denotes the phase of the complex variable Z, p2—the average of the logarithms of the phase of the impedance as measured by the signal electrode 13b ("middle") of FIG. 1 at the frequencies: 35, 40, and 45 MHz, namely $$p_2 = \frac{1}{3}\sum_{i=1}^{3} \log_{10}(\angle(Z_{el3}(f_i)))$$

$f_i = \{35, 40, 45\}$ MHz, p3—the average of the logarithms of the phase of the impedance as measured by signal electrode 14 of FIG. 1 at the frequencies: 100, 150, and 200 kHz, namely $$p_3 = \frac{1}{3}\sum_{i=1}^{3} \log_{10}(\angle(Z_{el1}(f_i)))$$

$f_i = \{100, 150, 200\}$ kHz, p4—the average of the logarithms of the magnitude of the impedance as measured by signal electrode 14 of FIG. 1 at the frequencies: 100, 150, and 200 kHz, namely $$p_4 = \frac{1}{3}\sum_{i=1}^{3} \log_{10}(|Z_{el1}(f_i)|)$$

$f_i = \{100, 150, 200\}$ kHz, p5—the square of the phase of the transmission coefficient as measured by the signal electrode 12a of FIG. 1 at the 2.02 GHz, namely $p_5 = (\angle(T_{el4}(2.02\text{ GHz})))^2$, with f1 as defined above being 2.02 GHz;

p6—the square of the phase of the transmission coefficient as measured by the signal electrode 12b of FIG. 1 at the 2.02 GHz, namely $p_6 = (\angle(T_{el5}(2.02\text{ GHz})))^2$, with f2 as defined above being 2.02 GHz;

p7—the temperature measured in close proximity of the tissue by temperature sensor 35.

Figure 5:
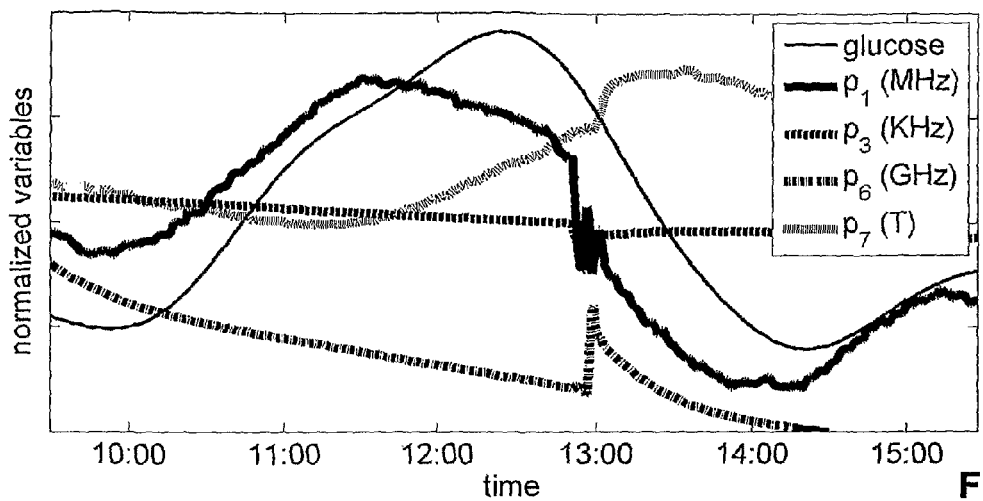
FIG. 5 shows how glucose content in the biological tissue mainly affect electrical parameters from the second frequency range (p1) whilst not affecting the electrical parameters from the other two frequency ranges (p3 and p6)

The first two terms are directly proportional to the changes in the beta dispersion induced by the changes in glucose concentration in the tissue (cf. FIG. 5). The two separation gaps allow addressing different penetration depths, where the beta dispersion is differently modulated because of different blood vessel concentration along the skin profile (cf. FIG. 6).

Figure 7:
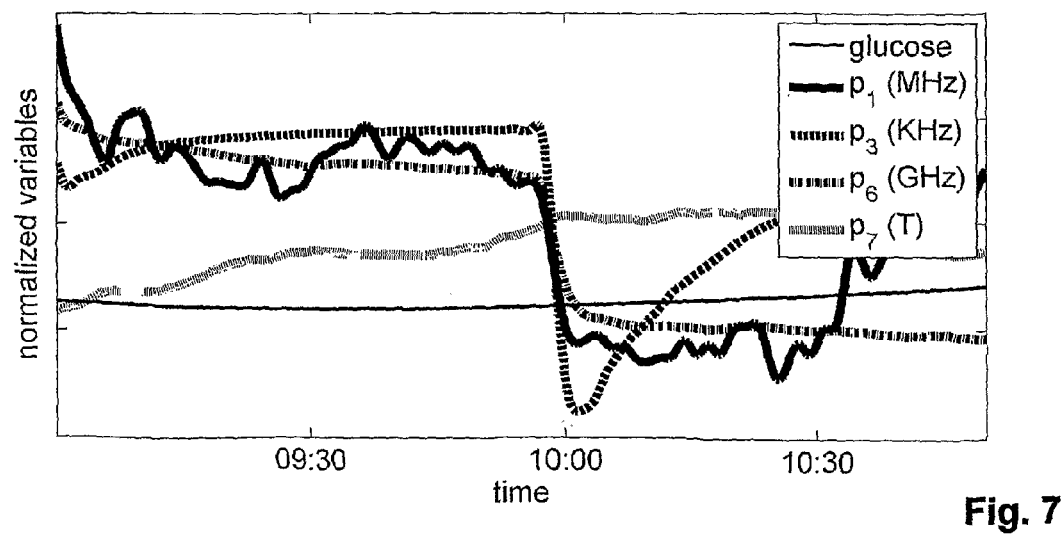
FIG. 7 shows a change in the state of the biological tissue consequent to a sweat event, occurring at about 10:00, the electrical parameters from the first frequency range (p3) measures the change induced at the surface, the electrical parameters from the third frequency range (p6) measures the consequent change in the water content in the biological tissue, the electrical parameters from the second frequency range (p1) are affected by a combination of these.

The third and fourth terms are necessary for accounting and compensating changes in impedance due to sweat events but unrelated to changes in glucose (cf. FIG. 7 for $p_3$, similar dependencies are observed for $p_4$).

Figure 8:
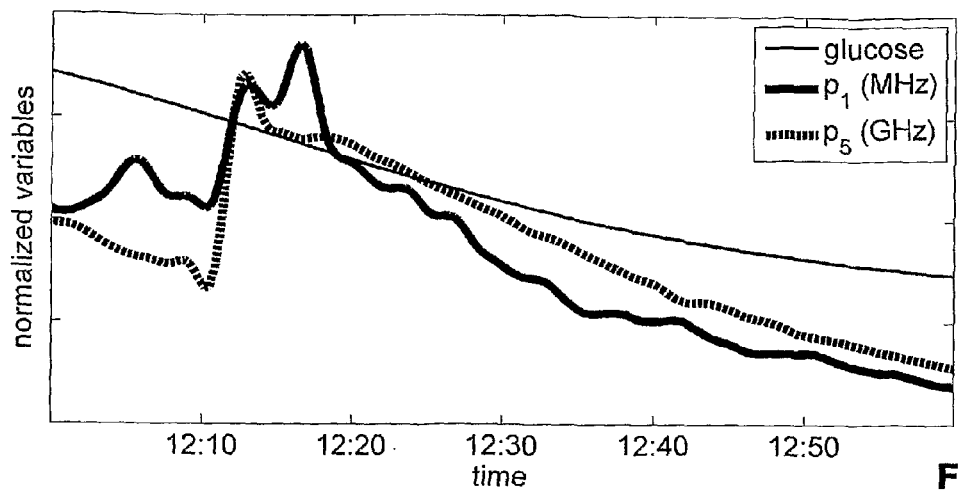
FIG. 8 shows a change in the state of the biological tissue consequent to a change in water content, occurring at about 12:10, which is measured by the electrical parameters from the third frequency range (p5) and affects the electrical parameters from the second frequency range (p1)

The fifth and sixth terms are necessary for accounting and compensating changes in impedance due to changes in the water content of the skin but unrelated to changes in glucose (cf. FIG. 8 for $p_5$, similar dependencies are observed for $p_6$). Again, the two separation gaps allow addressing the water content distribution which is not constant along the skin profile (cf. FIG. 9).

Figure 10:
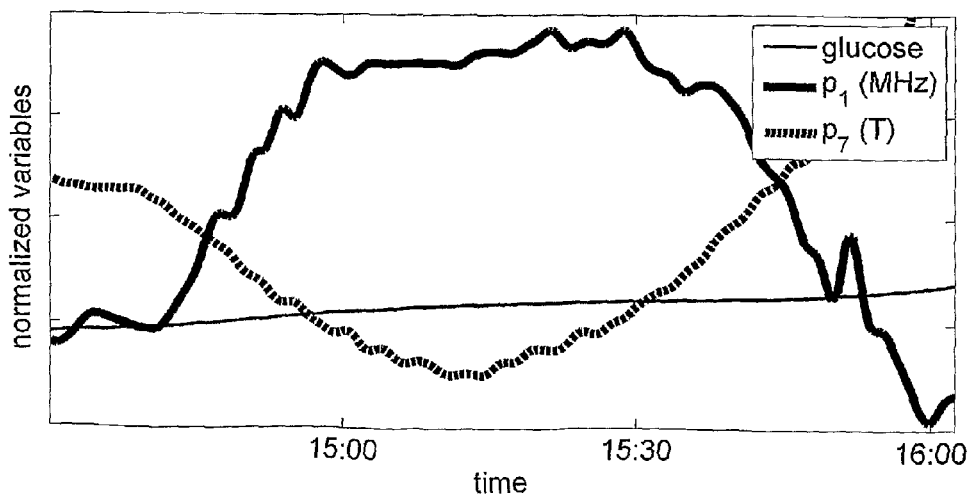
FIG. 10 shows the dependency of the electrical parameters from the second frequency range (p1) upon temperature (p7).

The seventh term is necessary for accounting and compensating changes in impedance due to changes in temperature of the skin but unrelated to changes in glucose (cf. FIG. 10).

Advantageously, the glucose estimation can be further refined by considering also the following terms, namely by expanding the combination as follows $c+k_1 \cdot p_1+k_2 \cdot p_2+k_3 \cdot p_3+k_4 \cdot p_4+k_5 \cdot p_5+k_6 \cdot p_6+k_7 \cdot p_7++k_8 \cdot p_8+k_9 \cdot p_9+k_{10} \cdot p_{10}+k_{11} \cdot p_{11}+k_{12} \cdot p_{12}+k_{13} \cdot p_{13}$, where the first eight terms (from c to $k_7 \cdot p_7$) are the same as described above. The weights coefficient $k_i$ (i=8 . . . 13) are similarly determined via calibration to reference measurements as described below, and the measured parameters $p_i$ (i=8 . . . 13) are as followings.

p8—the average of the logarithms of the phase of the impedance as measured by signal electrode 13a of FIG. 1 at the frequencies: 15, 20, and 25 MHz, namely $$p_8 = \frac{1}{3}\sum_{i=1}^{3} \log_{10}(\angle(Z_{el2}(f_i)))$$

$f_i = \{15, 20, 25\}$ MHz, p9—the average of the logarithms of the phase of the impedance as measured by the signal electrode 13b ("middle") of FIG. 1 at the frequencies: 15, 20, and 25 MHz, namely $$p_9 = \frac{1}{3}\sum_{i=1}^{3} \log_{10}(\angle(Z_{el3}(f_i)))$$

$f_i = \{15, 20, 25\}$ MHz, p10—the average of the logarithms of the magnitude of the impedance as measured by the signal electrode 13a of FIG. 1 at the frequencies: 0.5, 1, 2, and 5 MHz, namely $$p_{10} = \frac{1}{4}\sum_{i=1}^{4} \log_{10}(|Z_{el2}(f_i)|)$$

$f_i = \{0.5, 1, 2, 5\}$ MHz, p11—the average of the logarithms of the magnitude of the impedance as measured by the signal electrode 13b ("middle") of FIG. 1 at the frequencies: 0.5, 1, 2, and 5 MHz, namely $$p_{11} = \frac{1}{4}\sum_{i=1}^{4} \log_{10}(|Z_{el3}(f_i)|)$$

$f_i = \{0.5, 1, 2, 5\}$ MHz, p12—the magnitude of the transmission coefficient as measured by signal electrode 12a of FIG. 1 at the 1.10 GHz, namely $$p_{12}=|T_{el4}(1.10\text{ GHz})|,$$

with f1' as defined above being 1.10 GHz;

p13—the magnitude of the transmission coefficient as measured by signal electrode 12b of FIG. 1 at the 1.10 GHz, namely $$p_{13}=|T_{el4}(1.10\text{ GHz})|,$$

with f2' as defined above being 1.10 GHz;

p8 and p9 allow better characterizing the modulation of the beta dispersion due to glucose concentration changes, whilst all other terms allow accounting and compensating for changes in the electrical dispersive properties of the tissue which are unrelated to glucose changes.

Experimental Results

The above comments on the properties of the various parameters refer to enclosed FIGS. 5-10. These figures show the measured values of the respective parameters as well as of a invasively measured glucose level as a function of time.

Figure 6:
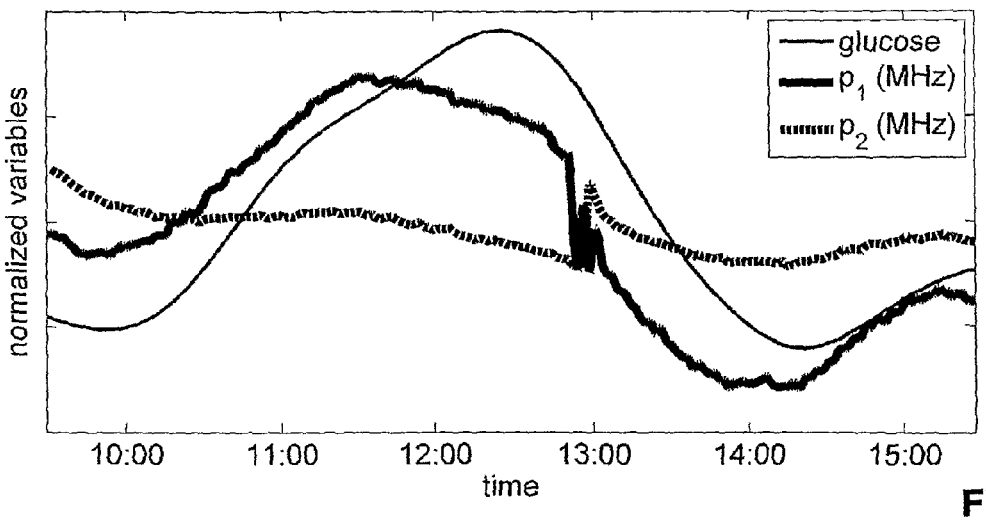
FIG. 6 shows how glucose modulates electrical parameters from the second frequency range (p1, p2) differently at different penetration depths because of different blood vessel concentration along the skin profile.

Study Procedure FIG. 5/FIG. 6/FIG. 8/FIG. 10:

The patients arrived in the clinical study unit in the morning. An intravenous (i.v.) insulin infusion was established and the Multisensor attached to the upper arm by an expandable band (proximal/distal location). After a run-in period of 75 minutes during which the glucose level was stabilized at an euglycaemic level, glucose was administered orally to induce one hyperglycaemic excursion. Euglycaemia was re-established by an i.v. insulin infusion.

In order to assure close blood glucose (BG) monitoring, changes in the BG were measured with a reference standard technique (HemoCue Glucose Analyzer) from intravenous blood samples.

Figure 9:
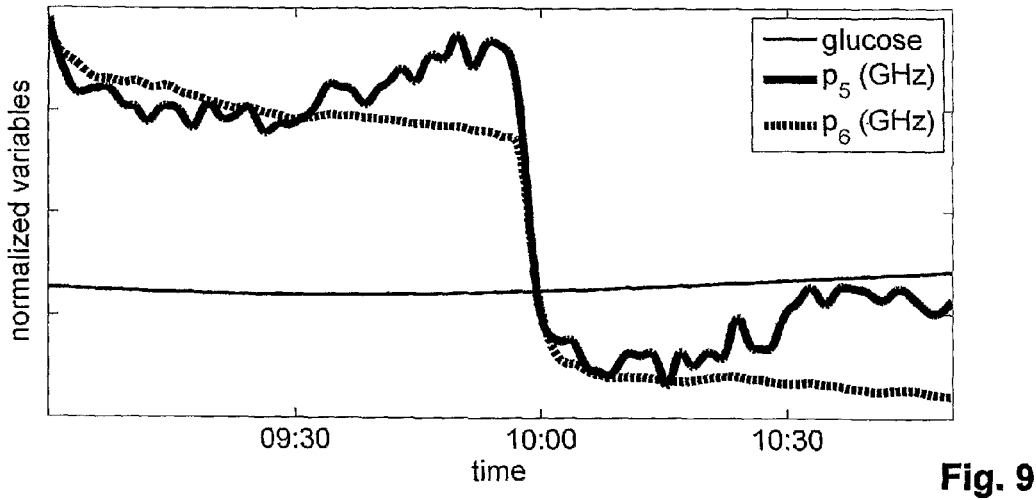
FIG. 9 shows that a sweat event, that leads to changes in water content, occurring at about 10:00, modulates electrical parameters from the third frequency range (p5, p6) differently at different penetration depths because water content distribution is not constant along the skin profile.

Study Procedure FIG. 7/FIG. 9:

The patients have worn the Multisensor on the upper arm during the day time at home or work. No glucose excursions were induced, but normal daily glucose variations were present.

The patients have performed frequent self monitoring of blood glucose (SMBG) of at least 10 finger pricks per day with a standard blood glucose meter (BGM).

Events FIG. 5/FIG. 6:

The patient was lying in bed in hospital.

13:00 h: The Multisensor was detached and reattached to the skin.

Events FIG. 7/FIG. 9:

The patient is at home and possibly active.

10:00 h: The patient is sweating. The sweat on the skin surface and moisture balance in the skin are both affected. No physical exercise during that time.

Events FIG. 8/FIG. 10

The patient was lying in bed in hospital.

12:10 h: The patient is changing his position. The water/tissue balance in the skin is affected.

14:30 h: The room temperature and therefore also the skin temperature drops.

Calibration

Here follows a description of the calibration using "run3" (which is now called $c_j$ in the claims.

The calibration of the coefficients ki (i=1 ... 7 or i=1 ... 13) can be performed as following.

Measurement data (p1 to p7 or p1 to p13) and the corresponding reference glucose values are collected across several days at a regular interval of one measurement every hour. The data are first divided into sub-series of 4 hours each, then, terms of the type $$c_j + \sum_{i=1}^{N} k_i \cdot p_i$$

are fitted, with respect to the coefficient ki, in least square sense to the reference glucose values, where a different additive constant cj is allowed for each sub-series. The use of several additive values allows compensating for a drift in the measurement by minimizing the effect of this latter in the estimation of the parameters $k_i$.

Afterwards, the determination of the glucose level in "normal" operation is performed as following.

First, a measurement of a reference glucose value is collected in the morning concurrently with a measurement set from the device, i.e. values of the parameters p1 to p7 or p1 to p13. With these measurements the offset c is determined by subtracting from the reference glucose value the weighted sum of the parameters weighted with the weights obtained in the calibration step described above.

After computation of the offset, for subsequent measurements during the rest of the day, the glucose level is computed from the measured parameters, the weights obtained in the calibration step, and the offset c.

Notes

The above description as well as the claims mention that a voltage is generated by the signal generation circuit. This formulation is not meant to restrict the signal generation circuit to a voltage source controlled to provide a given voltage, but it may also be a current source controlled to provide a given current, or it may be any other circuit generating a voltage giving rise to a current in the tissue.

As mentioned above, the device can also be equipped with optical sensors. The signals, or the logarithms of the signals, measured by these sensors can also be incorporated as further parameters p14, p15 in the linear combination of parameters for determining the glucose level.

Various of the parameters described above are determined from an average of measurements at different frequencies. Alternatively, a weighted sum can be used for the same purpose, wherein the weights can e.g. be obtained in a fitting process varying the weights in order to fit the calculated glucose level to a sufficiently large number of experimentally measured reference glucose levels.

Alternatively to the magnitude and phase parameterization of the electrical properties, the real and imaginary parts can be considered instead.

Advantageously, fitting criteria alternative to the least square can be considered, e.g. least absolute deviation, max absolute deviation, robust least squares, and regularized least squares.

While there are shown and described presently preferred embodiments of the invention, it is to be distinctly understood that the invention is not limited thereto but may be otherwise variously embodied and practiced within the scope of the following claims.

The invention claimed is:

1. A device for measuring a glucose level in living tissue, said device comprising
an electrode arrangement to be applied against said tissue,
a signal generation circuit, wherein said signal generation circuit is connected to said electrode arrangement in order to generate an AC signal voltage in said electrode arrangement,
a measuring circuit for measuring a response of said tissue to a field generated by said electrode arrangement due to said signal voltage,
a first temperature sensor generating a first temperature signal indicative of a temperature of said tissue,
a control unit for operating said signal generation circuit, wherein said control unit is structured and adapted to operate said signal generation circuit and said measuring circuit at least at a first frequency for measuring a first electric parameter, at a second frequency for measuring a second electric parameter and at a third frequency for measuring a third electric parameter, wherein said first frequency is in a first frequency range between 1 kHz and 200 kHz, said second frequency is in a second frequency range between 0.2 MHz and 100 MHz, and said third frequency is in a third frequency range of at least 1 GHz,
wherein said control unit is further structured and adapted to derive said glucose level from a combination of at least said first, second and third electric parameter and said first temperature parameter, and
wherein said control unit is structured and adapted to determine said glucose level from all of the following parameters p1-p7:
p1—a value depending on the phases of the impedances measured at several frequencies in the second frequency range at frequencies larger than 30 MHz, measured by means of an electrode pair having a separation gap of at least 2 mm,
p2—a value depending on the phases of the impedances measured at several frequencies in the second frequency range at frequencies larger than 30 MHz, measured by means of an electrode pair having a separation gap of less than 2 mm,
p3—a value depending on the phases of the impedances measured at several frequencies in the second frequency range at frequencies larger than 100 kHz,
p4—a value depending on the magnitudes of the impedances measured at several frequencies in the second frequency range at frequencies larger than 100 kHz,
p5—a value depending on the phases of the transmission coefficient measured at at least one frequency in the third frequency range, measured by means of an electrode pair having a separation gap of at least 1 mm,
p6—a value depending on the phases of the transmission coefficient measured at at least one frequency in the third frequency range, measured by means of an electrode pair having a separation gap of less than 1 mm, and
p7—a value depending on the temperature.

2. The device of claim 1, wherein said third frequency range is between 1 GHz and 30 GHz.

3. The device of claim 1, wherein said control unit is structured and adapted to operate said signal generation circuit and said measuring circuit to measure several electric parameters at different frequencies in said first frequency range and/or to measure several electric parameters at different frequencies in said second frequency range and/or to measure several electric parameters at different frequencies in said third frequency range.

4. The device of claim 1, wherein said electrode arrangement comprises a pair of first electrodes, wherein said first electrodes are interdigital electrodes and wherein said control unit is structured and adapted to measure said first electric parameter by means of said first electrodes.

5. The device of claim 4, wherein said electrode arrangement comprises a second pair of electrodes separated by a gap of at least 2 mm and wherein said control unit is structured and adapted to measure said second electric parameter by means of said second pair of electrodes.

6. The device of claim 5, wherein said electrode arrangement comprises at least two pairs of electrodes for measurements at said second frequency range, wherein said at least two pairs of electrodes have different gap widths, and wherein said control unit is structured and adapted to measure at least two electric parameters with said at least two pairs of electrodes at said second frequency range.

7. The device of claim 5, wherein said electrode arrangement comprises a third pair of electrodes and wherein said control unit is structured and adapted to measure said third electric parameter by means of said third electrodes, and in particular wherein said third pair of electrodes forms a coplanar waveguide.

8. The device of claim 7, wherein said electrode arrangement comprises at least two pairs of electrodes for measurements at said third frequency range, wherein said two pairs of electrodes have different gap widths, and wherein said control unit is structured and adapted to measure at least two electric parameters with said at least two pairs of electrodes at said third frequency range.

9. The device of claim 1, wherein said control unit further comprises a second temperature sensor for measuring a second temperature electric parameter indicative of a temperature within said device.

10. The device of claim 1, wherein said control unit is structured and adapted to calculate logarithms of the parameters p1, p2, p3, p4 and/or to calculate squares of the parameters p5 and p6.

11. The device of claim 1, wherein said control unit is structured and adapted to determine said glucose level further from at least one of following parameters p8-p13:
p8—a value depending on the phases of the impedances measured at several frequencies in the second frequency range between 10 and 30 MHz, measured by means of an electrode pair having a separation gap of at least 2 mm,
p9—a value depending on the phases of the impedances measured at several frequencies in the second frequency range between 10 and 30 MHz, measured by means of an electrode pair having a separation gap of less than 2 mm,
p10—a value depending on the magnitude of the impedances measured at several frequencies in the second frequency range at frequencies smaller than 10 MHz, measured by means of an electrode pair having a separation gap of at least 2 mm,
p11—a value depending on the magnitudes of the impedances measured at several magnitudes in the second frequency range at frequencies smaller than 10 MHz, measured by means of an electrode pair having a separation gap of less than 2 mm,
p12—a value depending on the magnitudes of the transmission coefficient measured at least one frequency $f1'<f1$ in the third frequency range, measured by means of an electrode pair having a separation gap of at least 1 mm, and/or
p13—a value depending on the magnitudes of the transmission coefficient measured at least one frequency $f2'<f2$ in the third frequency range, measured by means of an electrode pair having a separation gap of less than 1 mm.

* * * * *